United States Patent [19]
Smith

[11] Patent Number: 5,350,374
[45] Date of Patent: Sep. 27, 1994

[54] TOPOGRAPHY FEEDBACK CONTROL SYSTEM FOR PHOTOABLATION

[76] Inventor: Robert F. Smith, 3714 Henley Dr., Pittsburgh, Pa. 15235

[21] Appl. No.: 33,329

[22] Filed: Mar. 18, 1993

[51] Int. Cl.$^5$ ............................................. A61B 17/32
[52] U.S. Cl. ........................................... 606/5; 604/4; 604/11
[58] Field of Search .................. 606/4, 5, 6, 10, 11; 364/413.14, 413.23; 356/398, 392, 393, 394, 125, 51

[56] References Cited
U.S. PATENT DOCUMENTS
5,029,220  7/1991  Juday ........................................ 606/6

*Primary Examiner*—Peter A. Aschenbrenner
*Assistant Examiner*—Sonya C. Harris

[57] ABSTRACT

Real time feedback control during photorefractive keratectomy of individually ablated rasterstereographically imaged corneal areas; totality of these areas sufficient in number to result in a postoperative optically smooth epithelialized cornea. Novel micromechanical laser radiation modulating device means together with high speed digital control using specialized algorithms enabling a feedback control cycle of 0.2 second.

17 Claims, 7 Drawing Sheets

TOPOGRAPHY FEEDBACK CONTROL SYSTEM FOR PHOTOABLATION

BACKGROUND OF THE INVENTION

This invention relates to an apparatus and method, for performing either photorefractive keratectomy (PRK) or phototherapeutic keratectomy (PTK) on the anterior surface of the cornea of the eye using a feedback-controlled segmented laser beam.

The now widely recognized property of the excimer laser operating at a wavelength of 193 nm to ablate corneal stromal tissue has given rise to a number of inventions for controlling this radiation in a manner to reshape the full optically effective anterior surface of the cornea. These inventions include: en face methods where the depth of ablation is proportional to the intensity of radiation and duration of application; and tangential methods where ablation depth is a primarily a function of the axial position of the cornea relative to the region of laser radiation. Despite significant differences among the various methods and their apparatuses, they all lack the capability of being able to rapidly measure the topography of the cornea and based on these measurements modify the laser radiation pattern continually throughout the photoablation process. Contained in prior art are many claims for apparatuses and methods for controlling the ablation process through computer conducted feedback control—e.g. U.S. Pat. Nos. 4,941,093, 4,724,522, 4,729,372. Primarily two problems militate against the effectiveness of these techniques. The first is in the limitation of the keratometry techniques used to measure surface topography of the cornea because of the diffuse surface of the cornea undergoing ablation; the second limitation lies in the inability of these techniques to control the laser beam cross sectional intensity profile in response to instant by instant changes in the corneal topography. Means for surmounting these limitations are envisioned by the present invention.

Present state-of-the-art excimer lasers achieve beam cross sectional intensity uniformity to within about 5%; additionally, en face apparatuses deliver the radiation in the form of expanding or contracting circular or elliptical projections that are very accurately calculated and controlled to achieve desired ablation depths. Notwithstanding these controls, the standard deviation from desired for most PRK test groups with less than 5 D (diopters) of preoperative myopia is 1 D, implying a deviation of some 1/5=20% from the desired result which is some 4 times higher than the inherent accuracy (5%) of the procedure. Further, scanning electron microscope photographs of ablated corneas evidence surface irregularities some 8 to 10 times larger than preoperative corneas. These results suggest an inherent nonlinearity in the ablation of the corneal tissue and that regardless of how uniform the radiation reaching the cornea is, the ablated cornea will always depart from the nominal desired post operative goal.

Existing techniques for topographical measurement (keratometry) of the full anterior surface of the cornea are based upon either reflection or projection of reference light patterns. Because the removal of the epithelium from the cornea prior to PRK results in exposing the stromal corneal surface which is not optically reflective, keratometry techniques based upon reflection are unsuitable. However, research has found that projective techniques utilizing rasterstereographic imaging such as the PAR Technologies Corneal Topography System (U.S. Pat. No. 4,995,716) has successfully been used on deepithelialized and freshly keratectomized corneas. The PAR CTS projects a grid on the cornea which is then imaged by a video camera, digitized and analyzed to produce a tabulation of corneal elevations versus corneal diameters by means of algorithms that require about a half minute to compute by a 486 50 Mhz equivalent computer.

Although the PAR CTS can measure corneal surfaces to within an accuracy of about 0.1 diopter which is within the limit for achieving complete refractive correction of the human eye, it can be useful in terms of the present invention only if it can be made to operate in conjunction with an apparatus that modulates the cross sectional intensity of the laser beam so that once a measurement is made on a region of the cornea, it can be compared with a desired calculated value and the intensity of the laser corresponding to the said region be changed to achieve the desired value. Such a procedure, to be successful, must make measurements and supply the corrective action to a modulated laser beam many times over the duration of the ablation process—perhaps as often as every laser pulse.

Recent developments in the field of three-dimensional integrated micromechanical structures (U.S. Pat. No. 4,918,032) and in constructing leaf spring switches (U.S. Pat. No. 4,681,403), and in fabricating bending joints (U.S. Pat. No. 4,953,834) enable a means for modulating a light beam. Existing modulators are limited in regard to application to the present invention in that they are either based upon reflection (rather than transmission) or are limited in efficiency. It is therefore one object of this invention to provide a micromechanical structure that functions by modulating transmitted laser radiation and doing so efficiently.

The recent advent of high speed low cost computers along with high speed analog to digital conversion devices afford a means for implementing a system for photoablative topographical control that until recently, would have been either too expensive and/or physically impossible. Accordingly, it an object of this invention to implement such a system using the available technology.

SUMMARY OF THE INVENTION

It is the overall object of this invention to provide apparatus and method to photoablate the cornea by subdividing the cross section of a laser beam into a multiplicity of beams for each of which there shall be a corresponding cross sectional area on the cornea, said beams shall each correspond to a unique intersection of a grid of dot marks projected onto the stroma of the cornea and cover the optically useful surface of the cornea, the positions of these dot marks being imaged by a video camera, digitized, sent to a computer where the instantaneous corneal topography is computed and compared to a desired topography by which intensity modulation of the subdivided laser beams controls the photoablation to force the measured topography to conform with the desired topography. The apparatus of the invention shall consist of: A micromechanical modulating device consisting of a square or circular array of tiny movable masks that block or transmit the sub beams; an optical device for projecting a grid image onto the cornea; a video camera focussing on the cornea to produce a raster image; an analog-to-digital converter which digitizes each pixel of the raster image; a dedicated digital preprocessor which analyzes each pixel to determine the three dimensional coordinates (topography) of the cornea; a computer which receives the coordinates and calculates their variance from a desired set of coordinates; which computer also performs trending of the coordinates and timing of the laser pulses to insure correct laser-cornea alignment and control the overall photoablation process to minimize traumatizing of unablated eye tissues.

The essence and novelty of the invention is the real-time control of the intensity of the subdivided beams of the laser radiation, each subdivided or sub beam being collinear/coincident with an associated dot mark projected onto the cornea so that regardless of the shape of the cornea the dot mark always remains in the center of the sub beam, the totality of cross sectional areas of the laser sub beams completely covering the cornea.

A further novelty of the invention is the ability to change the desired corneal topography coordinates in a series of small steps so that after only a few laser pulses the actual cornea is ablated to a new, intermediate corneal shape. Such a gradual process avoids any excess errors from occurring in the ablated surface in the progression towards the ultimate target surface.

Within the essential structure of the invention, many different embodiments are possible, The preferred embodiment is constrained to present technology and, accordingly, comprises: 1) a projection grid comprising about 2000 dot marks, 2) a 193 nm argon fluoride excimer laser pulsing at a nominal 10 Hz rate, 3) a micromechanical modulating device to segment the laser beam into the same number of sub beams as there are grid dot-marks and provide a means for blocking and unblocking each sub beam, 4) a dielectric mirror transparent to the light of the projection system and fully reflective of the laser radiation, said mirror to enable the collinear alignment of the collimated rays of the projection system with the collimated sub beams of the laser, 5) a video camera imaging the cornea onto a one million pixel charge coupled device or vidicon tube, 6) an analog to digital converter converting the intensity of each pixel into an eight bit binary number, 7) a dedicated digital preprocessor, 8) a 486 66 Mhz or 586 equivalent computer for performing analysis and controlling the micromechanical modulating device through a digital to analog converter.

Alternate embodiments or modifications to the preferred embodiment include: 1) an optical means for diverging the laser beam in order to reduce its intensity before it, falls on the micromechanical modulating device and thereby avoid any possible damage to the device, followed by a converging and recollimating means that permits optimizing the cross section and spacing of the sub beams, 2) incorporating 193 nm transparent optical fibers into the micromechanical modulating device for the purpose of more efficient laser beam utilization, 3) using a micro binary/fresnel lens array in conjunction with optical fibers to obtain both efficient laser beam utilization and reduced intensity exposure, 4) a corneal positional detecting adjunct means for instantaneously detecting any corneal movement that could impact negatively on the functioning of the invention, 5) dispensing with the dielectric mirror in the preferred embodiment and directing the modulated laser beam collinear with the optical axis of the eye for performing either en face ablation or tangential ablation of the corneal surface, 6) combining the functions of the preprocessor and computer into a single parallel processing computer and/or utilizing digital signal processing hardware to further speed the topographic conversion of pixel intensity.

The basic procedure method of the invention involves the steps of: 1) curve fitting the topographically-measured coordinates of the preoperative cornea to produce a starting surface of revolution from which are generated a number of intermediate desired target surfaces, 2) comparing each intermediate surface with the corneal surface resulting in an error function that is used to set the modulation control of the laser beam, 3) pulsing laser, 4) comparing corneal surface with target surface again and if the error is reduced, introducing a new target and repeat through the final target surface.

Within the overall method of the invention are the algorithmic functions for 1) rapidly determining subsequent corneal topographies once the initial topography has been obtained, 2) relating the windows of the micromechanical modulating device to the projection system grid dot marks when the two beams are not collinear.

DETAILED DESCRIPTION OF THE INVENTION

Figure 1:
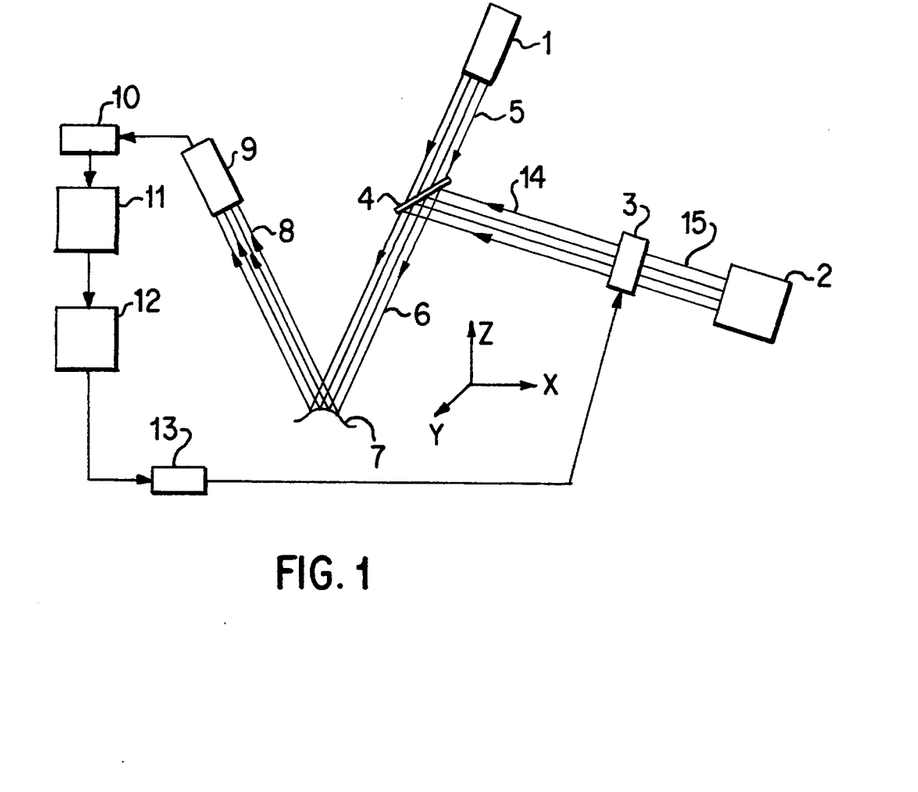
FIG. 1 shows a plan view of the primary components comprising a preferred embodiment of the invention.

FIG. 1 shows the components of a preferred embodiment apparatus. The projection system unit 1 incorporates a pulsed light source (e.g. xenon bulb) and optics which collimate the light and direct it at an angle of about 10° to 15° with respect to the optical axis of the cornea. The collimated light then passes through a reticle having a grid of lines or of circular dots (spaced about 0.2 mm apart), which produces the desired projected image through the beam 4 and covers the useful optical area of the cornea. By pulsing the light source, optimum brightness/contrast can be achieved in the projected image only in the time interval it is desired thereby avoiding excessive heating and energy consumption. Although the reticle is intended to produce a pattern of dark (low light intensity) circular dot marks equidistant from one another in a square pattern, other regular patterns of either dark or bright lines could be applicable.

Figure 2A:
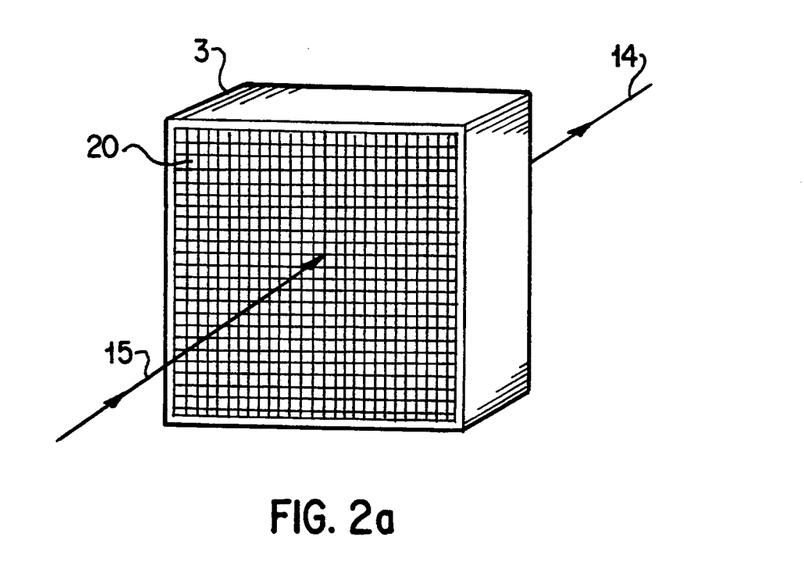
FIG. 2 shows the elements and function of the micromechanical modulating device in side and perspective views.

The source of photoablative radiation 2, an excimer laser or equivalent, is assumed to produce a collimated beam of radiation which is intercepted by a micromechanical modulating device 3. As seen in FIG. 2a, the device is composed of a square array of windows 20 each of which has a means for blocking or unblocking (masking or unmasking) the radiation 15, the windows forming collimated sub beams of radiation 14. These some 2000 windows, covering a total area of about 4 mm×4 mm, are capable of moving very fast to block or unblock the laser radiation because of their small size. Then by means of a dielectric mirror 4, which is transparent to the light in beam 5 but totally reflective (99%) to the laser radiation, beam 5 and sub beams 14 are merged into a combined beam 6 so that each projection beam dot mark passes through the center of each sub beam 14 cross section. This identical alignment of beams means that regardless of the shape of the cornea 7, wherever a dot mark is projected onto the corneal surface, it will always be surrounded by the laser sub beam. It is this characteristic that permits: 1) measurement of a surface spatial coordinate, 2) subtraction of this coordinate from a desired coordinate value to generate an error, 3) using this error to turn the sub beam either on or off. This negative feedback property has the theoretical capability of controlling the ablated shape of the cornea to within an error limited by the accuracy of the measurement process and the ablation depth caused by a single laser pulse. More practically, the ultimate refractive accuracy imparted to the cornea will be limited by unavoidable vibrations/motions, and the healing response of individual corneas.

When the visible (or wavelength greater than 193 nm) rays of the combined beam 6 fall upon the deepithelialized/keratectomized cornea 7, the video camera 9 detects the projected image on a charge coupled device or vidicon tube or similar image raster-generating device. There are one million picture elements (pixels) comprising the scanned image (raster frame). Each pixel is digitized by the high speed analog to digital converter 10 into an eight bit binary word and transmitted to the high speed digital preprocessor 11 by a direct memory access channel 16 in about 30 nanoseconds. So, from the time that the projection system 1 light source is strobed, one million bytes of sequential pixel data is stored in the memory of the preprocessor in about 30 milliseconds. Upon receiving the initial pixel array, the high speed digital preprocessor 11 (e.g. a 586 microprocessor having at least a two megabyte high speed cache memory) requires three or four seconds to completely process all one million pixel elements including the tasks of: precisely locating the video raster position of pixel intensity maxima/minima points, associating each of these points with the projection system dot mark that produced it, compensating for distortions in the video camera imaging, and finally calculating all of the fifteen hundred to two thousand coordinates comprising the topography of the cornea. Algorithms for accomplishing this have either already been patented (e.g. U.S. Pat. Nos. 4,995,716, 4,761,071) and/or are in the public domain. If this process of complete pixel processing had to be repeated for each pass of the feedback loop control cycle, the resulting delay could compromise the performance of the invention. To avert this problem, a simplified algorithm has been developed specifically for this invention that can reduce each succeeding topography calculation to less than 0.01 seconds once the initial topography calculation has been completed. The details of this algorithm appear later on in the methods description of the invention.

After the corneal coordinates are calculated in the preprocessor 11 they are transmitted to the computer 12 which has a 486 or 586 (or more powerful) equivalent engine. The highest priority tasks of the computer are: 1) measurement of the departure (error) of the corneal coordinates from one of a progression of predetermined conical surfaces of revolution and performing all of the translating and summing calculations, 2) sending the resulting control commands to the micromechanical modulating device 3 through the digital to analog converter 13. This task, requiring some 500,000 floating point operations is accomplished in less than 0.05 seconds, after which the computer is free to perform lower priority tasks such as trending, monitoring, display, etc.

Thus, in this preferred embodiment of the invention, the speed of the various components around the complete control loop permits a complete cycle to be completed in less than 0.2 second.

The size of each laser sub beam projection on the cornea (i.e 0.2×0.2 mm) was selected on basis of existing corneal stereographic systems. To answer the question as to whether this projection size is small enough to obtain adequate corneal optical smoothness, the following arguments are presented: If the sub beam intensity is so distributed so that the overlapping of adjacent beams results in uniform intensity, then no surface perturbations having the 0.2 mm period will occur; even if intensity and overlap is not perfect, the residual 0.2 mm period perturbations on the ablated cornea will be small enough so that when the epithelium reforms on the postoperative corneal stroma, the resulting projection of these perturbations through the epithelium will be negligible.

The principles of operation of electrostatically powered micromechanical structures and how they might relate to the present device 3 are discussed prior art. However, some customization is required for application to the present invention. In particular, among other characteristics, it is desired that: 1) the size of the individual windows in the micromechanical modulating device occupy as large a fraction of the area of the total array as possible in order to avoid excessive laser inefficiency, 2) that the materials comprising the array minimize ablation and heat buildup in the micromechanical modulating device, and 3) that the speed of masking-/unmasking the windows be as high as possible.

Figure 2B:
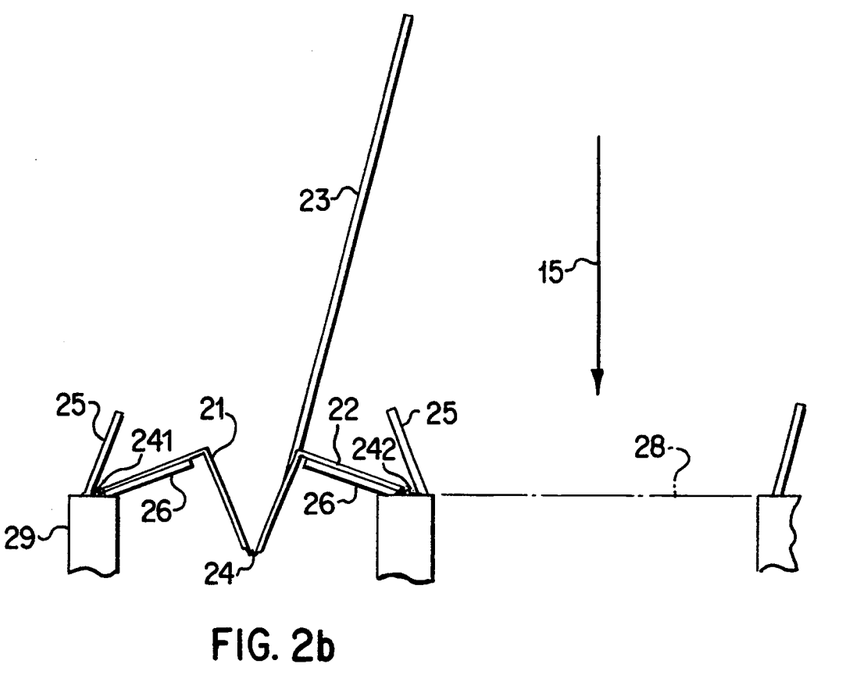
Figure 2C:
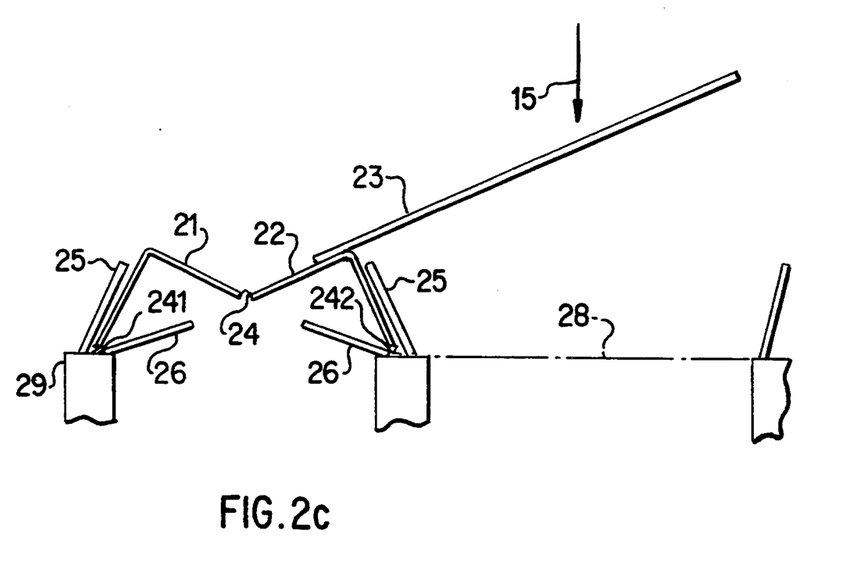
Figure 2D:
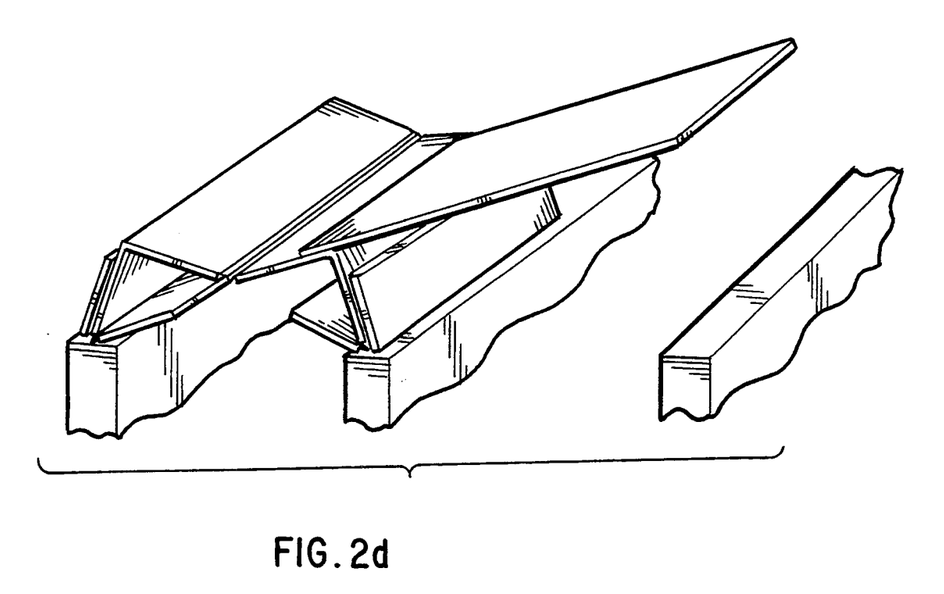

FIG. 2b shows an implementation of a micromechanical concept for achieving these characteristics. Because space must be provided for the mask actuating mechanisms and to insure sufficient strength of the supporting structure, the window areas 28 comprise only about 50% of the total cross sectional area of the device. The principle of operation of the actuating device is as follows: Two electrically conductive leaf spring microstructures 21 and 22 having a "V" or tent shape are joined together by a flexible movable joint 24. The opposite ends of the leaf springs are hinged to the stationary structure 29 of the array through flexible stationary joints 241 and 242. As shown in FIG. 2b, applying an upward force to move the joint 24 vertically results in a compression of the springs which is resisted by a downward force at joint 24. As vertical motion continues, at some point this resisting force will reverse, rapidly driving joint 24 upward until leaf spring equilibrium is reached as shown in FIG. 2c. Thus the mask 23 attached in cantilever fashion to leaf spring 22 will be tilted downward to block the radiation 15 through the window 28. Conversely if, in FIG. 2c, joint 24 is forced downward, the oppositely directed resisting force will reverse at the same vertical position as before, and the joint 24 will be driven rapidly downward resulting in mask 23 being tilted upward thereby unmasking the window 28 and permitting the passage of radiation 15. The desired initiating force at joint 24 is obtained by simultaneously electrically charging the leaf springs 21, 22 and the conducting stationary plates 25 and 26. In order to maximize electrostatic force effectively driving joint 24, an insulating layer of only about 1 micrometer separates leaf springs and plates when they are in close proximity. Applying voltages of opposite polarities to charge the plates 25 and 26, respectively, and changing the polarity of the voltage to charge the leaf springs, permits a means to force the mask into the desired position. For example, in FIG. 2b, applying a negative voltage to the springs, a negative voltage to plates 26 and a positive voltage to plates 25 will result in a large repulsive force between the springs and plates 26 causing mask 23 to be tilted to block or close window 28 as shown in FIG. 2c. In FIG. 2c, the application of a positive voltage to the springs causes the repulsion to occur between the springs and plates 25 tilting mask 23 to unblock or open window 28. In effect, a bistable or flip-flop mechanism has been devised permitting two stable states for the position of mask 23. FIG. 2d gives a perspective view of the micromechanical modulating device. The width of leaf springs 21, 22 and conducting plates 25, 26 are as wide as is allowed by fabrication limitations. The reason for this is to maximize the spring surface conducting plate area in order to maximize the electrostatic repulsion force. Although the window has been designated as being square, it could be made rectangular to maximize efficiency. However, this would result in a zonal rectangular projection of laser radiation on the cornea which would be incompatible with the square grid of dot marks from the projection system. If the grid of dot marks were made similarly rectangular, then the rectangular masks would be suitable. Another factor in sizing the windows of the micromechanical modulating device involves how the laser radiation sub beams will project on the cornea. If the sub beams were perfectly collimated and diffraction did not exist, then the ablated cornea surface would resemble a honeycomb because of the gaps between zonal radiation patterns. Fortunately, the effect of diffraction is such that there is a spreading of the 0.14×0.14 mm sub beam emerging from a window of the micromechanical modulating device so that after traveling about three inches, the sub beam cross section is spread out to an area somewhat greater than 0.25×0.25 mm. Because the intensity of the sub beam is reduced around its peripheral projection on the cornea, adjacent sub beam overlap results in a more or lees uniform intensity over the corneal surface.

The dielectric strength of available insulating materials (e.g. silicon dioxide) permits the application of about 5 volts to charge the spring and plate structures of the micromechanical modulating device. Because of the small mass of the springs and mask, the window close to open or open to close transition can be accomplished in some 10 microseconds, so the applied voltage pulses would be of this same duration. To avoid having one wire to control each mask, i.e. 2000, a matrix technique known in the art is resorted to, requiring only two times the square root of the number of windows, i.e. 90 wires, whereby all leaf springs in a given column of windows of the micromechanical modulating device are permanently electrically connected together giving X position selection, and all the plates in a given row of windows are electrically connected together giving Y position selection. Then by applying a voltage pulse of the same polarity simultaneously to the wires of a given column and row, the window always changes state. A problem with this arrangement is that the state of a window cannot be set without preknowledge of the existing state of each window. This limitation can be precluded by the use of an additional wire for each row. Here, by connecting all stationary plates to be positively charged (plates 25) in a given row, and by a separate common electrical connection all stationary plates to be negatively charged (plates 26) in a given row, the desired state of the window may be selected. So, to cause a selected mask transition, three simultaneous voltage pulses are applied: one pulse to a selected column wire with a positive polarity to open a window or negative polarity to close a window, a second pulse of positive polarity to the positive designated wire (for plates 25) of a selected row, and a third pulse of negative polarity to the negative designated wire (for plates 26) of the same selected row. This technique requires that only one such triplet of pulses at a time be transmitted by the digital to analog converter 13, If every window in the micromechanical modulating device 3 were to be pulsed, the time required would be about 2000×0.000010=0.02 second. This time can be greatly reduced by pulsing only those windows that need to change state.

The fabrication of the micromechanical modulating device 3 involves three-dimensional silicon photolithography; such techniques are covered in prior art. Also in prior art is covered the methods whereby aluminized magnesium fluoride can be deposited on the structures of the micromechanical modulating device exposed to laser radiation resulting in a reflection of some 95% of the energy away from the device.

Figure 3:
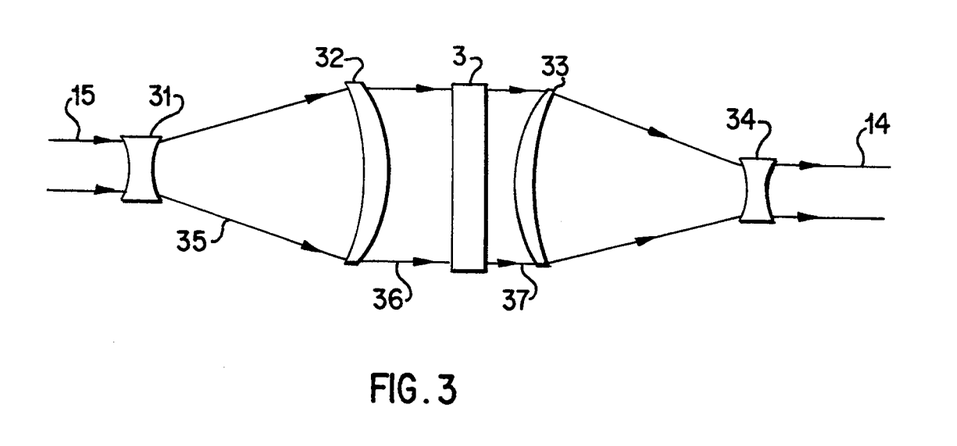
FIG. 3 is a side view of a lens based means for reducing radiation intensity exposure on the micromechanical modulating device.

An alternate implementation for the micromechanical modulating device is shown in FIG. 3. Here, the laser beam 15 is first passed through a diverging lens 31 producing a divergent beam 35 which is intercepted by converging lens 32 resulting in a recollimated beam 36 of reduced intensity which in turn is modulated by the micromechanical modulating device 3 where the resulting beam 37 is converged by lens 33 and then recollimated by diverging lens 34. This scheme has the advantage of being able to reduce the intensity falling on the micromechanical modulating device 3 to below the threshold of ablation and/or heat damage. Also the positioning of the lenses permits a precise adjustment of the cross sectional dimensions of the beam 14. Further, the scheme permits optimizing the size of the micromechanical modulating device 3.

Figure 4A:
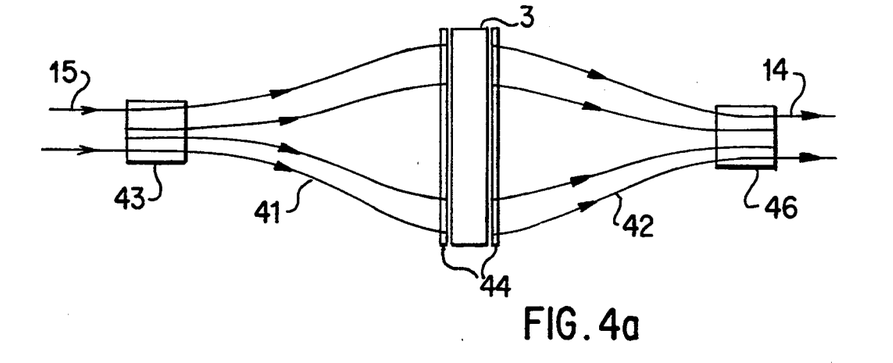
FIG. 4 shows a fiber optic means for maintaining high radiation efficiency and optimizing the sizing of the micromechanical modulating device; also a microlens means for reducing intensity.

A means for avoiding losses in laser efficiency is shown in FIG. 4a. Here, the laser beam falls axially upon the ends of transparent optical fibers 41 which are bundled together at 43 and then spread apart before being inserted into the axially-directed holes of an alignment plate 44. Thus the radiation leaving each fiber falls only on the window (movable mask) areas to avoid potential damage to other parts of the micromechanical modulating device 3. Alignment plate 45 aligns fibers 42 collinearly with the fibers 41 after which the fibers 42 are inserted into a third alignment plate 46 that maintains positional correspondence of the fibers 42 with the array of windows in the micromechanical modulating device 3 and hence the emerging sub beams 14. A refinement detail regarding the fibers 42 is to use graded-index fabrication which can minimize the divergence of the sub beams 14 to insure that the cross sectional area of impingement on the cornea provides just the right amount of overlap among adjacent sub beam projections.

Figure 4B:
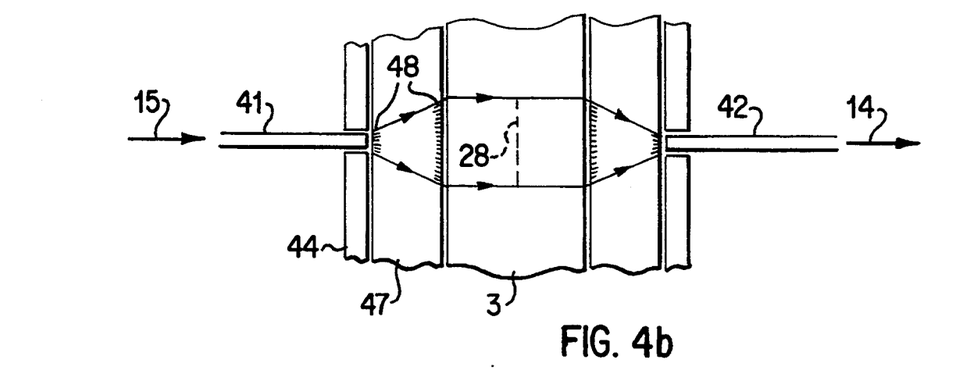

While the fiber optic scheme of FIG. 4a solves the problems of radiation inefficiency and exposure of the entire micromechanical modulating device to radiation, the problem of the full laser intensity (i.e, energy per unit area) falling on the masks of the micromechanical modulating device still exists. One remedy for this is found in the application of the newly emerging technology of binary optics as illustrated in FIG. 4b. Here silicon dioxide (or optical equivalent) substrates 47 are sandwiched between the alignment plates 44 and micromechanical modulating device 3. Then a matrix of fresnel-like micro lenses 48 is deposited on each side of the substrate 47 where the micro lens in proximity with the optic fiber 42 causes the radiation to be diverged to the other side of the substrate where a converging fresnel-like lens collimates the reduced intensity radiation and sizes the cross section of this collimated reduced intensity radiation to either completely pass through each window 28 or be blocked by the mask of the micromechanical modulating device 3. The radiation sub beams emerging from the micromechanical modulating device 3 are reconverged, recollimated (and re-intensified) by the corresponding structure on the other side of the micromechanical modulating device.

In the preferred embodiment of FIG. 1, the maintenance of alignment of the measurement beam 5 with the laser sub beams 14, greatly facilitates the speed and accuracy objectives of the invention. A possible disadvantage of this innovation is that because of the requirement that the measurement beam 5 be inclined (in the horizontal plane) to the axis of the cornea, the size of the incremental areas and hence the intensity that each of the laser sub beams project on the cornea will vary from one portion of the cornea to another. However, because of ability of the invention to modulate (switch on or off) each of the laser sub beams many times a second, changes in zonal intensity over the surface of the cornea can be compensated for, and thus this intensity variation is not fatal to the objects of the invention. Further, it is a simple matter to selectively attenuate those sub beams more directly falling upon the cornea so that the intensities of all incremental areas are held substantially constant. Nonetheless, because of the high versatility permitted by the computing elements of the invention, the collinearity requirement of laser sub beams 14 and the measurement beam 5, is not essential. For example, if the laser sub beams 14 were to be aligned with the axis of the cornea, the pattern of measurement beam dot marks would not correspond to the same pattern of incremental areas caused by the laser sub beams, but will vary depending on the position and shape of the cornea, However, once a coordinate on the cornea is determined, then it is a relatively simple computational procedure to determine which laser sub beam or combination of sub beams fall in this region of the cornea. Although the burden on the digital hardware (e.g. preprocessor and computer) is increased, it is manageable within the scope of the hardware discussed herein.

This computational capability also permits the insertion of an optical device into the modulated beam 14 for the purpose of performing tangential photoablation, In this case each sub beam will be deflected, by refracting and/or reflecting means, obliquely upon the cornea. Although correlating the projection of the laser sub beams on the cornea with the measurement grid of dot marks will be more computationally complex than for en face ablation, it is still feasible.

To this point in the description of the invention, it has been implicitly assumed that no corneal motion will occur between the instant a cornea 1 topography measurement is made and the pulsing of the modulated laser beam. Such a condition can be largely achieved by placing a vacuum (Thornton) ring around the in vivo cornea and mechanically fixing the ring to the frame of reference of the apparatus of the invention. Even by such means, small motions of the cornea on the order of a tenth of a millimeter could deteriorate performance. Although the three-dimensional measurement capability can readily detect corneal motion much smaller than this and automatically compensate for this by means of the software every computational cycle, the problem is that between the time that a topography measurement is made, the required correction calculated and the laser pulsed, a transient displacement of the cornea could occur that in turn would cause a displacement of the ablation pattern. A continuation of such corneal motions on successive ablation pulses could give rise to an instability in the control process. In order to deal with this contingency, the following presents a technique which can determine whether the position of the cornea is within an acceptable band immediately before the laser is pulsed—i.e. within about a millisecond.

Figure 5:
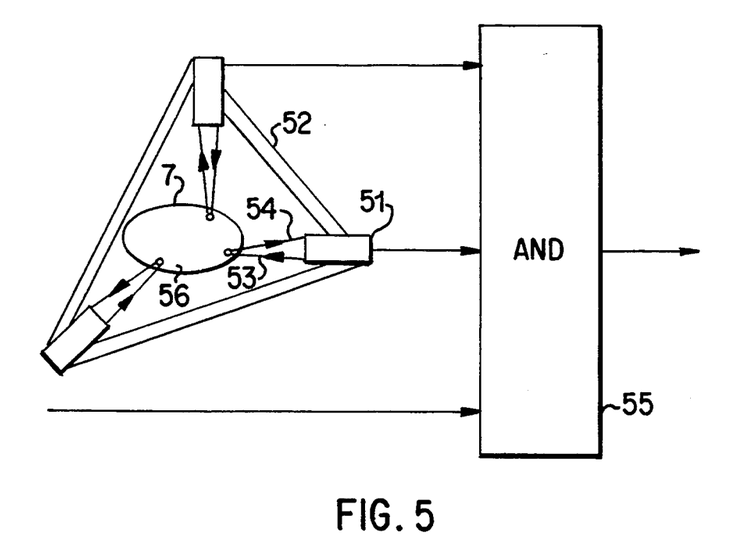
FIG. 5 shows an adjunct corneal positional detector device for inhibiting laser firing when the cornea is mis-aligned.

FIG. 5 shows a possible implementation of one such positional indicating device. It consists of three low intensity soft ultraviolet emitters/detectors 51 arranged orthogonally about the cornea 7 and rigidly interconnected by a frame 52 which in turn is rigidly connected to the frame of the apparatus of the preferred embodiment. Small quantities of fluorescein dye are injected into the periphery (non ablated region) of the cornea to form three separate dots 56, Each emitter/detector 51 emits a thin cone of ultraviolet light 53 whose cross sectional area at the cornea is about the same size of the fluorescein dot so that the intensity of the fluoresced light will drop rapidly as the uv light 53 is moved off the center of the dot 56. The emitter/detectors 51 each contain a small telescope that focusses the fluorescent light emitted by of the associated fluorescein dot onto a photovoltaic cell. Once all three emitter/detectors are aimed to bring the voltage outputs above a preset, near maximum threshold value, the voltage output of the AND circuit 55 steps to a value enabling the excimer laser 2 to fire. Movement of any one or more of the dots 56 beyond about a tenth of a millimeter inhibits the laser. Also the output of the AND circuit can be sent to a input port on the computer for monitoring/warning.

In concluding the discussion of apparatus, it is to be noted that digital hardware items have been specifically defined because they substantially achieve the objectives of the invention at relatively low cost with off-the-shelf availability. However, there is no intent of the invention to exclude any applicable hardware, digital or analog. Particularly, if it becomes desirable to achieve a shorter control cycle period and/or to increase the number of sub beams, etc., then substituting massively parallel processing digital hardware for the preprocessor and computer and/or including high speed digital signal processing hardware to accelerate the stereographic measurements, are techniques within the spirit of the invention. Such substitutions could so reduce the time period of the control cycle as to avoid the requirement of constraining the cornea and/or using the positional detection device thereby greatly simplifying the ablation procedure and shortening the duration of the operation.

With the foregoing description of the apparatus features of the invention, the methods and associated algorithms will now be described.

The following is a description of the procedure on an eligible candidate cornea: The cornea is deepithialized, fluorescein dye reference marks made, the head of the patient stabilized, the cornea constrained by a vacuum ring attached to the stationary frame of reference, nitrogen gas is directed onto the cornea for purposes of carrying away water vapor that could cause the surface to be reflective and interfere with measurements, and the positional indicating device (FIG. 5) aligned. Next, the topography is determined and from the 3-D coordinate points obtained, a series of meridional curve fits are obtained about the 0, 90, 135 and 225 degree axes of the cornea, using for example, the simplex algorithm of Nelder-Mead. Then, these 4 meridional curve fits are averaged to produce a rotationally symmetric starting reference surface. The shape of the human normal cornea is that of a conic surface of revolution given by the equation $$Z^2/a^2 \pm x^2/b^2 \pm y^2/b^2 = 1$$

where
- z is the distance along the optical axis of the cornea
- x is the horizontal distance along the 0° meridian—the nasal—temporal direction, anatomically
- y is the vertical distance along the 90° meridian—the inferior—superior direction, anatomically To make this equation more applicable in optical terms, a constant, SC (Schwarzchild constant), is defined whereby $$a = r/(1+SC) \quad b = r/(abs(1+SC))^{0.5}$$

where r=the paraxial radius of curvature; SC>0 for oblate ellipsoids, $-1 < SC < 0$ for prolate ellipsoids, SC=0 for spheroids, and SC<$-1$ for hyperboloids (requiring the sign of $b^2$ to be negative).

This formulation permits a convenient means for specifying the desired shape of the cornea. For example, if the preoperative average corneal surface shape is given by r=7.6 mm and SC=$-0.3$ and the desired postoperative surface is given by 8.2 mm and SC=$-0.6$, then if 12 intermediate reference surfaces are desired over the duration of the ablation process, the progression of radius of curvature will be: 7.6, 7.65, 7.7, 7.75 . . . 8.2, and for SC: $-0.3$, $-0.325$, $-0.35$, $-0.375$ . . . $-0.6$.

It is to be noted that the target or desired three-dimensional geometry of the corneal surface is not confined to conic surfaces of revolution, but allows for any aspherical surface, particularly those aspherics applicable to reducing presbyopia. Also, to compensate for astigmatism in the lens of the eye, compensating astigmatism may be incorporated in the desired target surface.

Figure 6A:
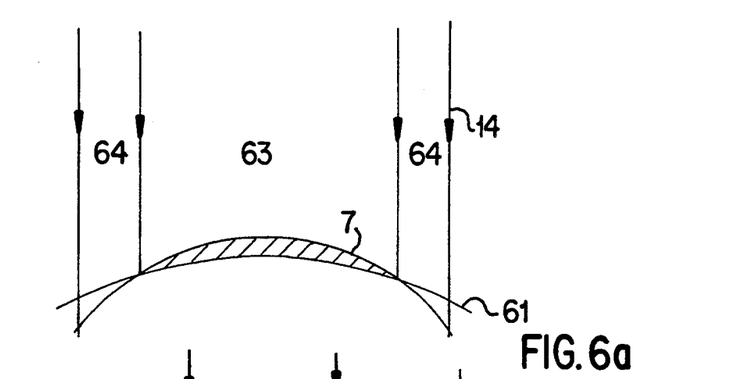
FIG. 6 illustrates the ablation action as it is controlled by the control methodology of the invention.
Figure 6B:
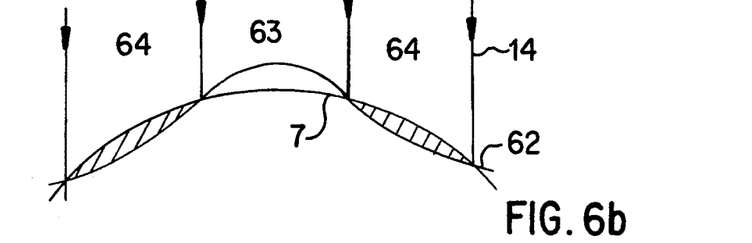

The area of the cornea to initially be ablated will normally depend on whether the target surface is shallower (myopia treatment) or steeper (hyperopia treatment), For myopia treatment the greatest depth of ablation will be at the center or apex of the cornea, while for hyperopia treatment the greatest depth of ablation will be in the peripheral region, FIG. 6 coarsely illustrates the action as it relates to the present invention: In FIG. 6a, for myopic correction, the apex of the target surface 61 has been moved below the apex of the corneal surface 7 so that in the region defined by 63, subtracting the target surface height (Z direction) from the corneal surface height (at the same X,Y coordinate) will result in positive surface error values. This axial subtraction process in the annular region 64 gives rise to all negative numbers. This will result in all the windows of the micromechanical modulating device 3 being opened exposing the circular cross sectional area spanned by 63, while the annular region 64 will be devoid of radiation because windows of the micromechanical modulating device corresponding to this region are closed. Hyperopic correction, FIG. 6b, shows the target surface 62 lying above the corneal surface, so that the axial subtraction process results in negative values about the apex region 63, while in the peripheral region 64, the values are positive resulting in the windows of the micromechanical modulating device being closed in the region corresponding to the apex region 63, and opened in the region corresponding to the annular region 64 thereby exposing that position of the cornea to radiation.

Figure 7:
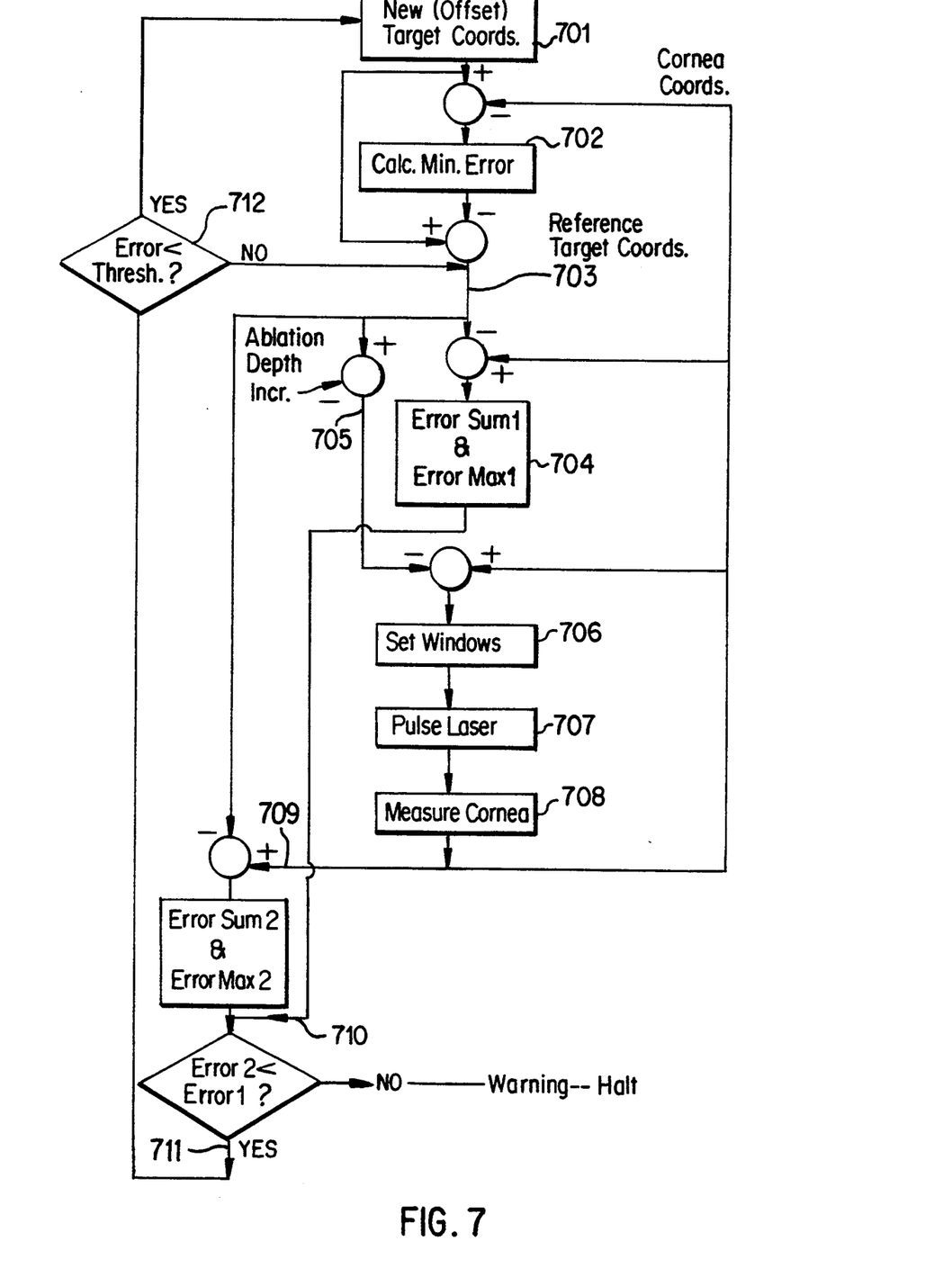
FIG. 7 is a flow diagram describing the real-time control algorithm of the invention.

Except for cases of very irregular astigmatism or keratoconus, the location of the apex of the cornea should not change over the course of the operation. Therefore, the axis of all intermediate target curves will be matched to that of the initially measured corneal surface. Once this is done, the target surface will be translated along this optical axis (Z-direction) until contact is made either with the corneal apex—in performing myopia correction, or near the corneal periphery—in the case of hyperopia correction. Within this general framework, the actual ablation procedure can begin:

FIG. 7 outlines the basic iteration procedure by use of the flow chart shown; the reference figures starting with the number 701 indicate the sequence of the consecutive steps. Starting by introducing a new target surface set of coordinates, the z values—also referred to as the axial or elevation values—of this new target surface will initially be offset several millimeters above the measured cornea coordinates. Next, for corresponding x,y coordinates, the elevation differences between target and cornea are formed and the minimum value determined is then used to translate the offset target surface to a reference target surface that just touches (intersects with) the cornea surface. (Note that this touching will be in the vicinity of X=0 and Y=0 for myopic correction, whereas for hyperopic correction it will be in the vicinity of a vector sum of X and Y value near to the periphery of the optically useful radius of the cornea, for example, 4 millimeters). Then, the absolute value of the axial differences of all the points between target and cornea are summed to produce a surface error sum which is stored together with the maximum difference or surface error. Next, the target surface is translated several micrometers into the corneal surface, and the windows of the micromechanical modulating device 3, corresponding to the zones where the target surface lies below the corneal surface, are opened. After the laser has been pulsed, subject to corneal position constraints, the cornea is remeasured, the same target surface is brought into contact as before, and the new surface error sum and maximum surface error compared with the previous values. If the surface error sum or maximum surface error are greater than the previous values, a warning is issued and the process is halted. If the surface error sum and maximum surface error are less than the previous values, these values are next checked to see if they are lower than a threshold value, and if so, the next intermediate target surface is introduced and the process repeated until the final target surface has been completed; otherwise the laser is pulsed again and the resulting cornea measurement compared with the same reference target surface.

Figure 8:
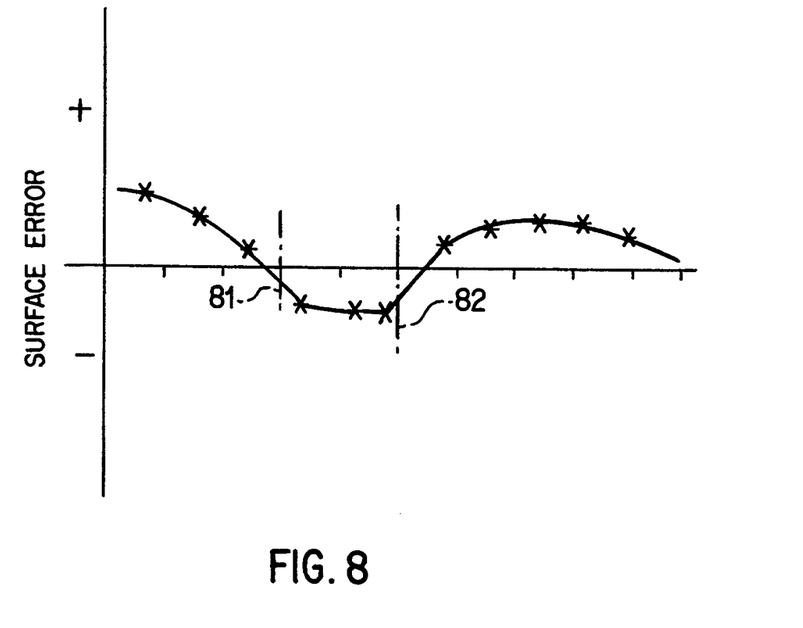
FIG. 8 illustrates a method for correlating non-coincident modulated laser radiation and measurement beams.

The embodiment of the invention, wherein the modulated laser beam is made collinear with the axis of the eye rather than with the projection beam, necessitates a continual correlating of the windows of the micromechanical modulating device with the measurement grid dot marks. Because the grid dot marks and the windows can be aligned to always coincide in the Y direction, the correlation process is only a function of variations in the X direction. In depiction of the method, FIG. 8 shows a plot, along a constant y value, of the differences between the z values of the corneal surface and the desired target surface for a succession of x values. Here the X axis is marked off every 0.2 mm, corresponding to the centers of a row of adjacent windows on the micromechanical modulating device. For the convention used, positive surface values signal the corneal zones to be ablated while negative surface error values indicate zones to be left unablated. The points on the curve marked with a * correspond to the points where the grid dot marks project onto the corneal surface. The algorithm connects these * points with straight line segments and causes windows to be masked or unmasked depending on whether the window center x values correspond to negative or positive surface errors, respectively. Because of the simplicity of the algorithm, the increase in computer control cycle execution time is small.

Figure 9A:
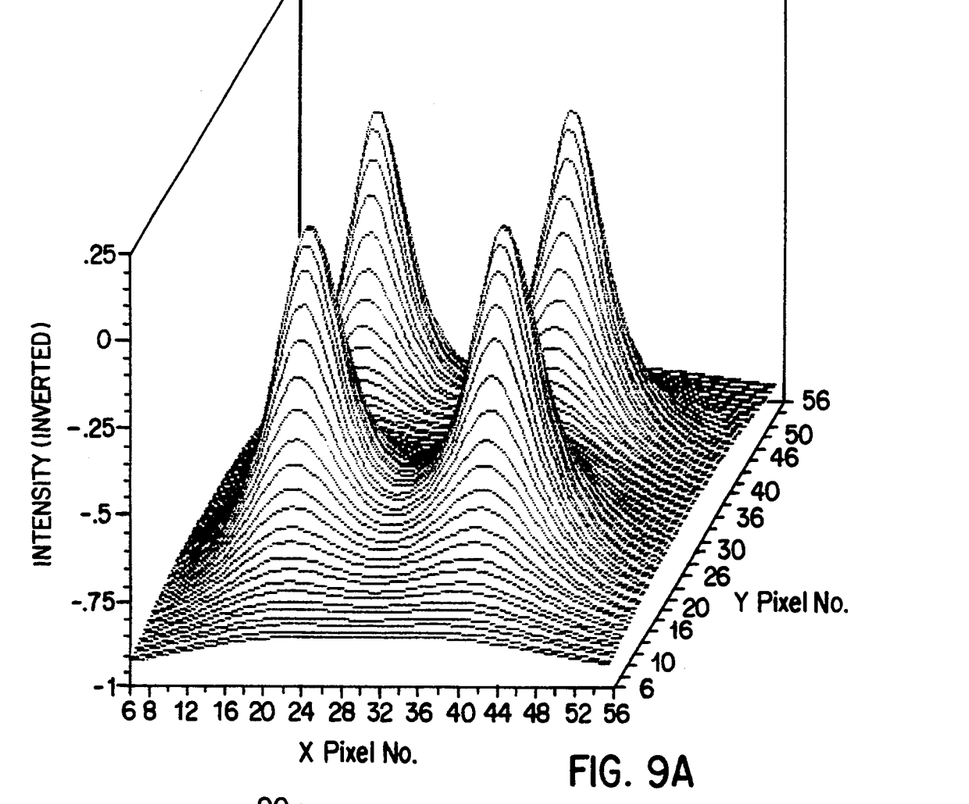
FIG. 9 illustrates a method for rapid stereographic conversion of pixel intensity data.
Figure 9B:
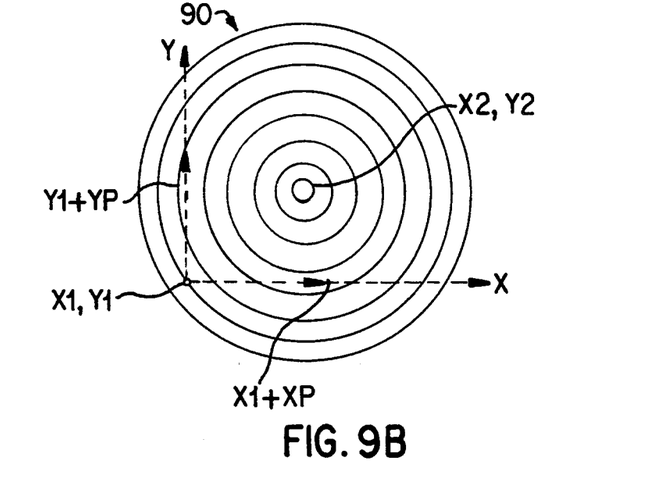

As discussed earlier, converting the pixel intensity data to the complete set of corneal three-dimensional coordinates is a very computer intensive process. However, once the initial corneal topography is solved, the fact that under normal conditions of the ablation process, topography changes from one control cycle to the next will be very small. FIG. 9a shows a typical pixel intensity distributed resulting from a group of four grid dot-marks. The gradual changes in intensity shown permit gradients—i.e. intensity change versus X and Y pixel change—to be readily calculated allowing a means of iterating in on intensity minimums, thereby locating the centers of the grid dot-marks. If the position of the intensity minimums from one topography measurement to the next change by less than half the distance between adjacent minimums, the new corneal surface coordinates can rapidly be calculated. FIG. 9b plots the contours 90 of constant intensity about a pixel intensity minimum located at the coordinate x2,y2. The previous pixel intensity minimum is shown at coordinate x1,y1. Now the algorithm for locating the new minimum begins by checking which direction reduces pixel intensity and then moving in that direction until a minimum is found, first along the x axis and then along the y axis. Given that the number of pixels travelled in the x direction is xp and the number travelled in the y direction is yp, a new pixel point is located at the coordinate x1+xp,y1+yp, and the procedure repeated until no change results at which time the new location of the imaged grid dot-mark has been found from which the new corneal surface coordinate can be calculated. It is noted that before calculating the new corneal coordinate, the coordinate of minimum intensity will be interpolated among several of the lowest intensity pixels in both x and y directions to maximize accuracy.

As previously mentioned, the computer has spare time between control cycles so that it can be charting the progress of all the ablation zones and if one or several is behaving erratically, these zones and how they have been trending can be displayed on the monitor as a caution or warning. Also, the entire control cycle history of the operation can be stored for usage in later correlation with the progress of the patient over time and also for developing a broad based statistical data base that may permit optimizing the procedure for all patients.

I claim:

1. An apparatus for performing photorefractive keratectomy on an anterior surface of a cornea comprising:
    a laser means for producing a collimated beam of photoablative radiation said beam having a cross sectional area;
    a modulating device having dividing means for subdividing said beam's cross sectional area into sub beams, said sub beams comprised of laser radiation covering an optically useful area of the cornea, said modulating device further comprises blocking means for either blocking or transmitting said radiation comprising said sub beams; an optical projection system comprised of a light source emitting visible light, said light being collimated and directed through a reticle, said reticle producing a grid of collimated rays equal in number to said sub beams;
    a dielectric mirror transparent to the light of said optical projection system, said mirror fully reflecting said radiation of said sub beams, said mirror collinearly aligning the collimated rays of said optical projection system with said sub beams to produce a combined beam, said combined beam being projected upon said cornea;
    a video camera for imaging said grid projected on said cornea onto a raster of pixels;
    an analog to digital converter for converting said light projected image of each said pixel into a binary word and transmitting said word through a direct memory access channel;
    a preprocessor containing a high speed microprocessor and memory, said preprocessor receiving and translating said words into three-dimensional corneal coordinates;
    a computer means receiving said corneal coordinates and generating an array of errors between said corneal coordinates and desired coordinates; a digital to analog converter generating said external control signals in response to said errors, said signals in turn controlling said modulating device.

2. An apparatus according to claim 1 wherein said modulating device is a micromechanical structure comprising a matrix of windows whereby each said sub beam is produced by a portion of said beam passing through said window on said micromechanical structure, said window comprising a movable mask allowing said sub beam to be blocked or unblocked, said mask attached to a spring structure, said structure comprising two tent shaped leaf springs having opposite sides, joined together through a flexible movable joint, said opposite sides of said leaf springs being hinged to said micromechanical structure through flexible stationary joints, said movable joint able to be translated spatially from a first stable position to a second stable position by applying an external force to said movable joint, said force being greater than a resisting force created by rotation of said springs about said stationary joints, two stationary plates extend from said stationary joints, one of said plates being inclined so that it is parallel and in close proximity with a side of said leaf spring when the flexible joint is in the first stable position, another of said plates being parallel and in close proximity to corresponding sides of said leaf springs when said flexible joint in the second stable position, where movement; of said movable joint causes said mask to be cantilevered thereby blocking or unblocking said window, said external force to cantilever said mask being supplied by electrostatically statically charging said plates and said springs resulting in a repulsive force when said plates and springs are in close proximity but not directly contacting one another.

3. The micromechanical modulating device of claim 2 wherein all said springs in a given column constituting said matrix of windows are electrically interconnected by wires, wherein said stationary plates in a given row are electrically interconnected by wires, where in order to block or unblock said radiation through a given window, said plates and said springs are electrically charged by application of a voltage pulse sent simultaneously to corresponding column and row wires;

4. The micromechanical modulating device of claim 3 in which blocking or unblocking of a window depends on voltage polarity of said voltage pulse applied to said row and column wires wherein polarity is changed via electrical interconnection of said wires.

5. The micromechanical modulating device of claim 2 where all portions of said structure exposed to said radiation are coated with aluminum magnesium fluoride to reflect away said radiation for protection of said device.

6. The apparatus according to claim 1 further comprising optical means for facilitating greater surface area of the micromechanical modulating device wherein said beam from said laser is diverged and recollimated by said lens means to produce reduced intensity radiation, said reduced intensity radiation being applied to said micromechanical modulating device producing reduced intensity sub beams, said reduced intensity sub beams are then converged and recollimated by further lens means to return the sub beams to desired intensity.

7. The apparatus according to claim 1 wherein the laser radiation beam is directed to a contiguously spaced bundle of optical fibers, said fibers being spread apart where each input fiber is aligned with a window of the micromechanical modulating device, out of said window said sub beam enters one of a second grouping of output fibers, said output fibers being brought together substantially contiguously to form said desired sub beam.

8. The apparatus of claim 7 wherein the laser radiation out of the input fibers is intercepted by an optical plate having micro fresnel-like lens structures resulting in the radiation from each fiber being diverged and recollimated into a larger cross sectional area of lower intensity radiation falling on the windows of the micromechanical modulating device, said reduced intensity radiation upon exiting said modulating device, enters a similar optical plate that converges and recollimates said radiation into said output fibers.

9. The apparatus according to claim 1 further including a positional detecting device for maintaining corneal alignment, said detecting device consisting of three emitters of soft ultraviolet light and three detectors of said light, said emitters directed orthogonally towards three small respective areas of fluorescent material embedded in the cornea, said three detectors focussing respectively on said areas and converting intensity therefrom to voltages, said voltages being fed to a thresholding AND circuit, said circuit either enabling or inhibiting said laser from firing.

10. The apparatus according to claim 1 where said dielectric mirror is removed and said sub beams directed axially towards the cornea.

11. The apparatus of claim 10 where an optical device intercepts said sub beams, said optical device either reflects of refracts said sub beams obliquely to said cornea.

12. The apparatus according to claim 1 where said computer means includes parallel processing digital hardware.

13. A method for performing photorefractive keratectomy on an eye comprising the steps of:
removing an epithelium of a cornea over an optically useful portion of the cornea and holding the eye immobile and providing detectors to inhibit laser pulsing if cornea is not in position;
projecting a collimated beam of visible light through a measurement grid of dot-marks upon said cornea, said grid projection on said cornea being imaged on a pixel defined raster of a video camera, said pixels being digitized and stereographically analyzed to produce a number of three-dimensional coordinates, said coordinates being equal to in number to said grid dot-marks and from said coordinates curve fitting a conic surface of revolution, generating a series of intermediate target surfaces, said intermediate surfaces starting with a curve fitted preablated cornea and gradually changing into a desired corneal surface;
subdividing a beam of photoablative radiation into a number of sub beams, aligning each of said sub beams with each said dot-mark projected through said collimated beam of visible light forming a combined beam, projecting said combined beam over said cornea;
controlling corneal ablation by: an iterative step comprising comparing cornea surface with one of saint intermediate target surfaces from which elevation differences or errors are generated, using these errors to direct said sub beams to be turned either on or off depending on whether said errors are positive or negative, ablating cornea with these controlled sub beams, measuring cornea and comparing with said intermediate target surface.

14. A method according to claim 13 where the step of controlling the ablation is further defined by the steps:
introducing a new set of intermediate offset target coordinates, determining a minimum difference between said target coordinates and said cornea coordinates, subtracting said minimum difference from said offset target; coordinates to get reference target coordinates, subtracting each said reference target coordinate from each corresponding said cornea coordinate giving a first error, summing said first errors giving a first error sum, determining largest first error;

selecting an incremental ablation depth, subtracting said depth from said reference target coordinates giving a set of ablation target coordinates, subtracting said ablation target coordinates from said cornea coordinates yielding a set of positive errors and negative errors, turning on said sub beams corresponding to said positive errors, turning off said sub beams corresponding to negative errors thereby subjecting the cornea to a short period said selective ablation;

measuring cornea to produce a new set of corneal coordinates, subtracting said reference target coordinates from said new cornea coordinates giving a second set of errors, summing absolute values of these errors giving a second error sum and getting a second error maximum, determining whether the said second error sum is less than said first error sum and whether said second error maximum is less than said first error maximum and if so, checking to see if second error is below a threshold error and if so, introducing next consecutive said offset target coordinates and iterating, and if not, iterating said steps with same said reference target coordinates; halting execution if said second error sum is larger than said first error sum or said second error maximum is larger than said first error maximum, 15. A method according to claim 13 where the iterative step is performed in less than 0.2 seconds.

16. A method according to claim 13 wherein the step of aligning each said sub beam comprises non-collinearly aligning each said dot-mark, further including the step of correlating nasal-temporal positions of said sub beam projections on the cornea with said grid dot-mark projections on the cornea, said correlating step consisting of connecting straight lines between coordinates defined by said positive and negative errors versus nasal-temporal coordinates corresponding to said grid of dot-marks, translating said nasal-temporal coordinates of the sub beams into equations formed by the straight line segments, turning said sub beams on if said errors are positive, turning said sub beams off if said errors are negative.

17. A method for rapidly converting a raster of pixel intensity data produced by repeated stereographic imaging of a corneal surface undergoing photoablation into three-dimensional coordinates defining corneal surface topography, said method being contingent on an initial set of coordinates defining said cornea, said method requiring that changes in topography of successive measurements result in a shifting of projected grid dot-marks projected on the corneal surface by less than one half of adjacent dot-marks separation, said method comprising the steps:

specifying previously determined raster coordinates corresponding to pixel intensity minimums, measuring a new raster of pixel intensity data, determining directions on the caster that reduce pixel intensity and then iteratively moving in those directions until new raster coordinates corresponding to the pixels of lowest intensity are found, determining via computer means from these new raster coordinates a new three dimensional topography of the cornea.

* * * * *